(12) United States Patent
Blumenfeld (10) Patent No.: US 11,508,465 B2
(45) Date of Patent: Nov. 22, 2022

(54) SYSTEMS AND METHODS FOR DETERMINING EVENT PROBABILITY

(71) Applicant: Clover Health, Jersey City, NJ (US)

(72) Inventor: Ian Blumenfeld, San Francisco, CA (US)

(73) Assignee: Clover Health, Jersey City, NJ (US)

(*) Notice: Subject to any disclaimer, the term of this patent is extended or adjusted under 35 U.S.C. 154(b) by 127 days.

(21) Appl. No.: 16/021,976

(22) Filed: Jun. 28, 2018

(65) Prior Publication Data

US 2020/0005910 A1 Jan. 2, 2020

(51) Int. Cl.
G16H 10/60 (2018.01)
G06N 7/00 (2006.01)
G06N 20/00 (2019.01)

(52) U.S. Cl.
CPC ............ G16H 10/60 (2018.01); G06N 7/005 (2013.01); G06N 20/00 (2019.01)

(58) Field of Classification Search
CPC .. G06N 3/00; G06N 5/00; G06N 7/00; G06N 20/00; G16H 10/60; G16H 40/00; G16H 50/00; G06Q 10/06
See application file for complete search history.

(56) References Cited

U.S. PATENT DOCUMENTS

| 9,235,332 B2* | 1/2016 | Poulin | G06F 3/0484 |
| 2006/0129427 A1 | 6/2006 | Wennberg | |
| 2008/0240425 A1* | 10/2008 | Rosales | G06F 21/6254 380/28 |
| 2010/0036884 A1* | 2/2010 | Brown | G06Q 30/00 706/21 |
| 2010/0076785 A1* | 3/2010 | Mehta | G16H 10/60 705/2 |

(Continued)

FOREIGN PATENT DOCUMENTS

| JP | 2014178800 A * | 9/2014 | G06Q 50/22 |
| WO | WO-2014201515 A1 * | 12/2014 | G16H 50/30 |

(Continued)

OTHER PUBLICATIONS

Lezzoni, MD; Lisa, et al. "Predicting In-hospital Mortality for Stroke Patients: Results Differ across Severity-measurement Methods". Medical Decision Making, 16(4), 348-356. Oct. 1, 1996. (Year: 1996).*

(Continued)

*Primary Examiner* — Christopher L Gilligan
*Assistant Examiner* — Chance L Smith
(74) *Attorney, Agent, or Firm* — Lee & Hayes, P.C.

(57) ABSTRACT

Systems and methods for data unfolding are disclosed. For example, it may be desirable or necessary to increase a data set, such as for increasing accuracy of one or more predictive models. Data set proliferation without introducing unnecessary bias may be important for increasing such accuracy. Described herein are system and methods that allow for data set proliferation by generating records based on whether an event occurred with respect to an entity during multiple time intervals. A record may be generated for each time interval and the associated data may be unfolded and disassociated, at least partly, from other records related to the entity. Those records may then be used for data analytics and/or predictive model generation, for example.

20 Claims, 5 Drawing Sheets

(56) References Cited

U.S. PATENT DOCUMENTS

| | | | |
|---|---|---|---|
| 2010/0076799 | A1* | 3/2010 | Magent .............. G06Q 30/0202 705/7.31 |
| 2011/0082712 | A1* | 4/2011 | Eberhardt, III ........ G06Q 10/10 705/4 |
| 2014/0207492 | A1* | 7/2014 | Farooq .................. G06Q 10/10 705/3 |
| 2014/0343439 | A1 | 11/2014 | Sweeney et al. |
| 2015/0193749 | A1 | 7/2015 | Ivanoff et al. |
| 2015/0370992 | A1* | 12/2015 | Yao ........................ G06Q 50/22 703/2 |
| 2017/0052958 | A1 | 2/2017 | Manning et al. |
| 2017/0091642 | A1* | 3/2017 | Enck .................... G06F 16/2477 |
| 2017/0103163 | A1 | 4/2017 | Emanuel et al. |
| 2017/0137498 | A1 | 5/2017 | Wollacott et al. |
| 2018/0046926 | A1* | 2/2018 | Achin .................... G06Q 10/04 |
| 2018/0082025 | A1* | 3/2018 | Hu ......................... G16H 50/70 |
| 2019/0034591 | A1* | 1/2019 | Mossin ................. G06N 3/0445 |
| 2019/0180358 | A1* | 6/2019 | Nandan ................ G06K 9/6282 |

FOREIGN PATENT DOCUMENTS

| | | | | |
|---|---|---|---|---|
| WO | WO-2018160929 | A1 * | 9/2018 | ......... G06F 16/2365 |
| WO | WO-2018228852 | A1 * | 12/2018 | ............. G16H 50/30 |

OTHER PUBLICATIONS

Jeffery, Alvin, et al. "Participatory design of probability-based decision support tools for in-hospital nurses". Journal of the American Medical Informatics Association, 24(6), 1102-1110. Jun. 19, 2017. (Year: 2017).*

Rivera, Edgardo, et al. "First-cycle absolute neutrophil count can be used to improve chemotherapy-dose delivery and reduce the risk of febrile neutropenia in patients receiving adjuvant therapy: a validation study". Breast Cancer Research, 5(5), R114-R120. Jun. 20, 2003. (Year: 2003).*

The PCT Search Report and Written Opinion dated Sep. 9, 2019 for PCT Application No. PCT/US2019/038572, 8 pages.

* cited by examiner

```
┌─────────────────────────────────────────────────────────────────────────────┐
│ Generate first record corresponding to person, first record including: first│
│ portion of data associated with first period of time; and first indication  │
│ of whether event occurred with respect to person during first period of time│
│                                    602                                       │
└─────────────────────────────────────────────────────────────────────────────┘
                                      ↓
┌─────────────────────────────────────────────────────────────────────────────┐
│ Generate second record corresponding to person, second record including:    │
│ second portion of data associated with second period of time; and second    │
│ indication of whether event occurred with respect to person during second   │
│ period of time                                                              │
│                                    604                                       │
└─────────────────────────────────────────────────────────────────────────────┘
                                      ↓
┌─────────────────────────────────────────────────────────────────────────────┐
│ Generate model configured to determine event probability, model fit based at│
│ least in part on first record and second record                             │
│                                    606                                       │
└─────────────────────────────────────────────────────────────────────────────┘
                                      ↓
┌─────────────────────────────────────────────────────────────────────────────┐
│ Determine, based at least in part on model, event probability associated    │
│ with group of people                                                        │
│                                    608                                       │
└─────────────────────────────────────────────────────────────────────────────┘
                                      ↓
┌─────────────────────────────────────────────────────────────────────────────┐
│ Rank individual people in group of people based at least in part on event   │
│ probability                                                                 │
│                                    610                                       │
└─────────────────────────────────────────────────────────────────────────────┘
```

FIG. 6

SYSTEMS AND METHODS FOR DETERMINING EVENT PROBABILITY

BACKGROUND

The use of data for analytics has become ubiquitous. The usefulness of data for analytics may depend, generally, on whether a sufficient set of data has been collected. However, in some instances, sufficient data has not been generated and/or has not been collected to provide a meaningful analysis. Described herein are improvements in technology and solutions to technical problems that can be used to, among other things, generate data sets of sufficient quantity and quality to increase the accuracy of data analytics.

BRIEF DESCRIPTION OF THE DRAWINGS

The detailed description is set forth below with reference to the accompanying figures. In the figures, the left-most digit(s) of a reference number identifies the figure in which the reference number first appears. The use of the same reference numbers in different figures indicates similar or identical items. The systems depicted in the accompanying figures are not to scale and components within the figures may be depicted not to scale with each other.

DETAILED DESCRIPTION

Systems and methods for folding and unfolding data are described herein. Take, for example, a system that has stored thereon and/or has access to one or more databases containing data, such as health-related data, for example. Such data may be used by the system for one or more purposes, such as predicting outcomes and/or events. However, without a robust data set from which to perform data analyses, the accuracy of such predictions may be limited. Increasing available data on which to perform analyses may improve prediction accuracy and/or allow for more robust analysis techniques to be utilized. For example, the system may have access to data for two patients. One of the patients may have been hospitalized since data was recorded for the patient while the other patient may not have been hospitalized. In these examples with just two data points on hospitalization, determining a likelihood that the patients and/or other patients will be hospitalized using the available data would likely lead to an inaccurate result. For example, this data may indicate that patients are 50% likely to be hospitalized during a certain period of time. This estimation may be grossly over or under predicted for a given population.

The presently-disclosed systems and methods may be utilized to increase data set size to increase data analysis accuracy without introducing bias from historical information. For example, the system may have access to data associated with multiple people. For each person, which may otherwise be described herein as an entity, a determination may be made as to whether an event of interest has occurred. By way of example, the data may indicate if each person has been hospitalized. In this example, for each person, only one data point exists for a hospitalization event, namely, the person either has or has not been hospitalized. To increase data points, the data for a person associated with the system may be "folded" as described herein. For example, a time interval may be selected at which to assess the data associated with the person. By way of example, the time interval may be 28 days. The system may then analyze the data with respect to the time intervals to determine if the event has occurred during that time period. For example, the system may determine that for a first time interval (i.e., the first 28-day period of data) the person was not hospitalized; for a second time interval (i.e., the second 28-day period of data) the person was not hospitalized; for a third time interval (i.e., the third 28-day period of data) the person was hospitalized; and for a fourth time interval (i.e., the fourth 28-day period of data) the person was not hospitalized. In this example, the folding of data may result in the generation of four records for the person in question. The first record may include data associated with the person (e.g., blood pressure, age, weight, etc.) for the first period of time and an indication that the person was not hospitalized. The second record may include data associated with the person for the second period of time and an indication that the person was not hospitalized. The third record may include data associated with the person for the third period of time and an indication that the person was hospitalized. The fourth record may include data associated with the person for the fourth period of time and an indication that the person was not hospitalized.

By folding data as described above and elsewhere herein, multiple records may be generated for each person associated with the system. In the example provided above, the original data record associated with the person, which indicates that the person was at some point hospitalized, may be utilized to generate four independent records with health-related data and their own indications of hospitalization events. These records may be "unfolded" or otherwise dissociated from each other and may be utilized to generate one or more models for, for example, determining an event probability. The models may be trained using the unfolded data and may be utilized to prospectively determine event probabilities for people associated with the system.

For example, a system may have access to health-related data for 20,000 people, which amounts to 20,000 records with one record for each person. Utilizing the data folding and unfolding techniques described herein, such as using 10 time intervals during the folding processes, 200,000 records may be generated and then utilized to generate prediction models. This more robust data set may increase the data sampling available to the prediction models, which may allow those models to be trained and/or fit more accurately. The models may be built utilizing, for example, one or more machine learning techniques where features associated with the health-related data are inputs to the model. The models may be utilized to determine a probability of an outcome occurring, such as for people associated with the system. Those people may be ranked based at least in part on the determined probability and the ranking may be utilized to, for example, generate a recommendation, intervention schedule, incentive program, and/or to admit or not admit people to a given program.

The prediction models generated utilizing the folding and unfolding techniques described herein may be validated using one or more validation techniques. For example, an area-under-the-resource-operating-characteristic-curve measurement may be utilized to gauge the accuracy of the model generated utilizing the unfolded data. In examples, the measurement may be at least 0.84, indicating a high degree of accuracy. Additionally, or alternatively, precision-recall characteristic measurements may be utilized to determine precision of the prediction models. The model generation techniques described herein may also include at least one of gradient boosting techniques and/or hyperparameter tuning.

Additionally, or alternatively, while the unfolded records may be independent of each other, an association between records belonging to the same person may be identified and utilized when performing model testing. In these examples, a group of records belonging to a first set of people may be used for training purposes while another group of records belonging to a second set of people may be used for testing purposes. By maintaining an association between records belonging to the same person, records may be split into the two groups without introducing leakage and/or overlap to the testing process.

Additionally, or alternatively, the systems and methods described herein may identify input features that increase the accuracy of the prediction models and other input features that decrease the accuracy of the prediction models or have no or little effect on the prediction models. The prediction models may be refit to utilize the features that increase accuracy while refraining from utilizing the features that decrease accuracy or have no or little effect on accuracy.

The present disclosure provides an overall understanding of the principles of the structure, function, manufacture, and use of the systems and methods disclosed herein. One or more examples of the present disclosure are illustrated in the accompanying drawings. Those of ordinary skill in the art will understand that the systems and methods specifically described herein and illustrated in the accompanying drawings are non-limiting embodiments. The features illustrated or described in connection with one embodiment may be combined with the features of other embodiments, including as between systems and methods. Such modifications and variations are intended to be included within the scope of the appended claims.

Additional details are described below with reference to several example embodiments.

Figure 1:
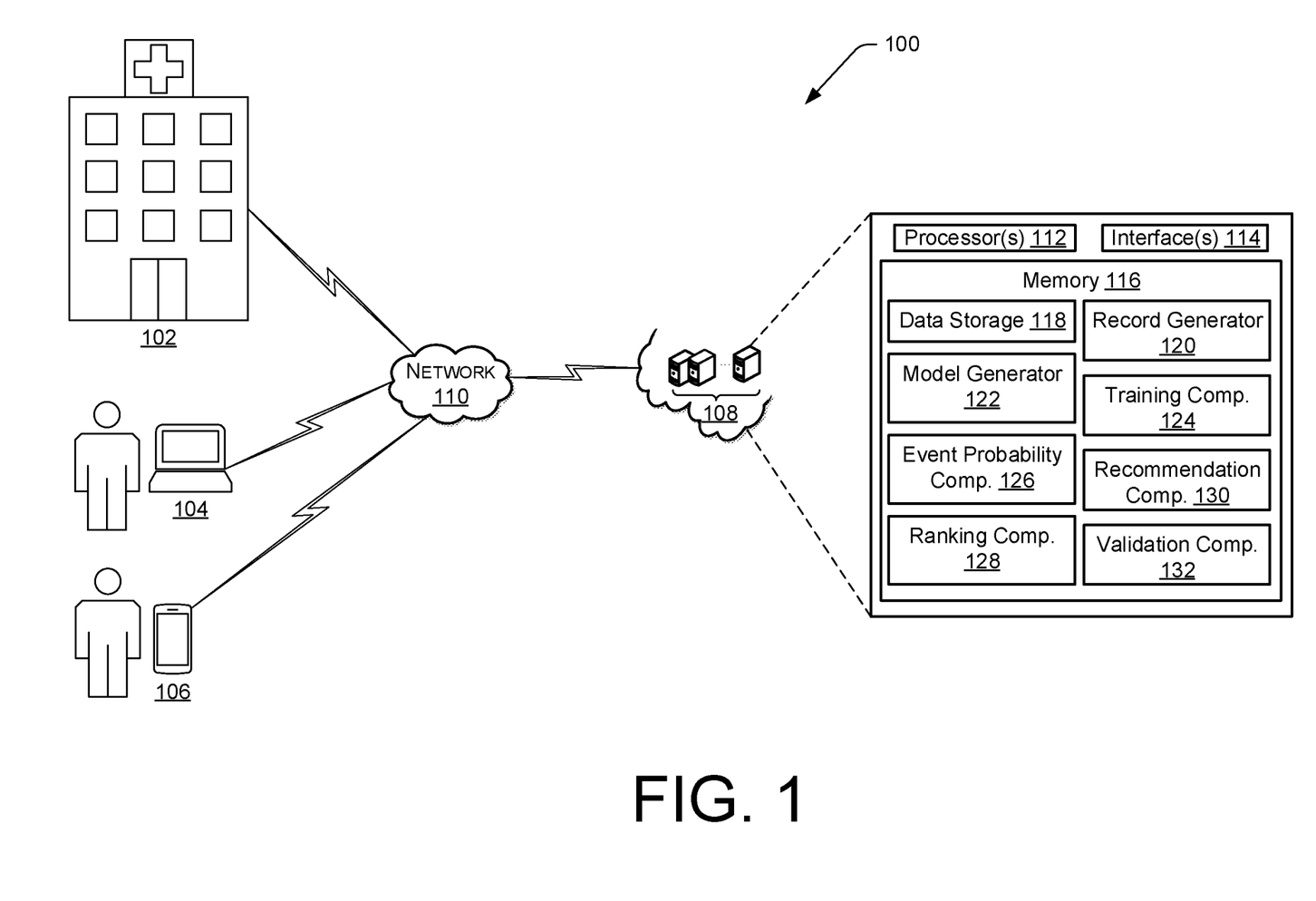
FIG. 1 illustrates a schematic diagram of an example environment for data folding and unfolding.

FIG. 1 illustrates a schematic diagram of an example environment 100 for data folding and unfolding. The environment 100 may include a first data source 102, a second data source 104, and a third data source 106, for example. As shown in FIG. 1, the first data source 102 represents a remote system that generates and/or acquires data associated with one or more people and stores that data, such as in a database associated with the first data source 102. By way of example, the first data source 102 may be a hospital, clinic, and/or other type of healthcare provider. The second data source 104 represents a personal computing device associated with a given person. The computing device may receive inputs from the person and may generate input data, which, in the examples provided herein, may be utilized to generate and/or store health-related data associated with the person. The third data source 106 represents a mobile device associated with another person. The mobile device may receive inputs from the other person and may generate input data, which, in the examples provided herein, may be utilized to generate and/or store health-related data associated with the other person.

It should be understood that while three data sources 102, 104, 106 are depicted in FIG. 1, the number of data sources may be one, two, three, or more than three. In examples, the number of data sources may be much more than three, such as thousands of data sources. It should also be understood that while the types of data sources have been depicted with respect to FIG. 1 as remote systems, personal computing devices, and mobile devices, the types of data sources may be any device that may receive input and generate data associated with a person based on that input. Further, while the examples provided herein are described with respect to data associated with a person or people, the data need not be specific to a person. For example, the data may be data associated with a device, a system, an entity that is not a person, an object, etc.

The first data source 102, the second data source 104, and/or the third data source 106 may communicate with a system 108 via one or more networks 110. The communication may include the sending and/or receiving of data associated with a person and/or people associated with a given data source. The communication may also include data representing recommendations and/or requests generated by the system 108, which may be based at least in part on the data as described herein. The system 108 may include one or more components, such as, for example, one or more processors 112, one or more network interfaces 114, and memory 116. The memory 116 may include one or more components, such as, for example, a data storage 118, a record generator 120, a model generator 122, a training component 124, an event probability component 126, a ranking component 128, a recommendation component 130, and/or a validation component 132. Each of the components of the memory 116 will be described below in detail.

The data storage 118 may be configured to store data received by the system 108. For example, the data storage 118 may be configured to receive data from one or more of the first data source 102, the second data source 104, and/or the third data source 106. The data storage 118, and/or one or more other components of the system 108, may be configured to format the data for storage in the data storage 118 such that the data is associated with an identifier of the person associated with the data. For example, data associated with a first person may be received from one or more of the data sources 102, 104, 106. Each data source 102, 104, 106 may send the data in the same or differing formats and/or may send the data with differing identification formats. For example, data for "John Smith" may be received from the first data source 102 with the identifier "John Smith," while data may be received from the second data source 104 with the identifier "J. Smith" or "Smith, John." The data storage 118 and/or other components of the system 108 may be configured to associate received data such that the data is associated with the proper person in the system 108. Additionally, or alternatively, while the data storage 118 has been described as storing data, the data storage 118 may also, or alternatively, be configured to request and/or access data from the data sources 102, 104, 106 with or without storing that data in the memory 116 of the system 108.

The record generator 120 may be configured to perform the folding and/or unfolding processes described herein. For example, the record generator 120 may be configured to identify, determine, and/or receive an indication of a time interval at which to generate records. Keeping with the example used herein, the time interval may be, for example, 28 days. It should be understood that this example time interval is used for illustration only. Other time intervals may be utilized. The record generator 120 may also be configured to identify, determine, and/or receive an indication of a period of time during which to generate records. For example, a particular time frame may be utilized to generate the records and/or an amount of time from a certain date may be utilized. For example, the record generator 120 may identify a one-year period of time during which to generate records. Alternatively, the record generator 120 may identify a date, such as Jan. 1, 2017, from which to start record generation either moving forward or backward in time.

The record generator 120 may be further configured to identify, determine, and/or receive an indication of the data sources from which to utilize data. For example, the record generator 120 may identify, determine, and/or receive an indication that the data storage 118 is to be utilized for receiving data. Additionally, or alternatively, the record generator 120 may identify, determine, and/or receive an indication that the first data source 102, the second data source 104, and/or the third data source 106 is to be utilized in addition to or alternatively to the data storage 118.

The record generator 120 may be further configured to identify, determine, and/or receive an indication of an event to analyze with respect to the data. For example, the record generator 120 may identify, determine, and/or receive an indication that an event of interest is hospitalization. The record generator 120 may then determine, for each time interval during the identified time period, whether the event occurred. For example, the system 108 may determine that for a first time interval (e.g., the first 28-day period of data) a particular person was not hospitalized; for a second time interval (e.g., the second 28-day period of data) the person was not hospitalized; for a third time interval (e.g., the third 28-day period of data) the person was hospitalized; and for a fourth time interval (e.g., the fourth 28-day period of data) the person was not hospitalized. In this example, the time interval was identified and/or determined to be 28 days, and the identified time period was 112 days. This process may be performed for all or some of the people on which data is available to the system 108. In examples, the system 108 may identify, determine, and/or receive an indication of the people, the number of people, and/or categories of people on which to perform the processes described herein.

In the example used herein, the folding of data as described above may result in the generation of four records for each person. For the example person illustrated herein, the first record may include data associated with the person (e.g., blood pressure, age, weight, etc.) for the first period of time and an indication that the person was not hospitalized. The second record may include data associated with the person for the second period of time and an indication that the person was not hospitalized. The third record may include data associated with the person for the third period of time and an indication that the person was hospitalized. The fourth record may include data associated with the person for the fourth period of time and an indication that the person was not hospitalized.

By folding data as described above and elsewhere herein, multiple records may be generated for each person associated with the system and/or each person selected for data folding. In the example provided above, the original data record associated with the example person, which indicates that the person was at some point hospitalized, may be utilized to generate four independent records with data and their own indications of hospitalization events. The records may be unfolded, or otherwise separated from each other as independent records for use by the system 108 as described herein. Extrapolating from the provided example, the system 108 may have access to data for 100,000 people, which amounts to 100,000 records with one record for each person. Utilizing the data folding and unfolding techniques described herein, such as using 10 time intervals during the folding processes, 1,000,000 records may be generated and then utilized by the system 108.

The model generator 122 may be configured to generate one or more models based at least in part on the records generated by the record generator 120 and/or other data available to the system 108. The more robust data set generated by the folding and unfolding techniques described herein may increase the data sampling available to the models, which may allow those models to be trained and/or fit more accurately. The models may be generated utilizing, for example, one or more machine learning techniques where features associated with the data are inputs to the model. The models may be utilized to determine a probability of an outcome occurring, such as for people associated with the system. These models may be described herein as predictive models and/or predictive layers.

A predictive model may include one or more models that utilize predictive analytics to determine one or more outcomes. Predictive analytic techniques may include, for example, predictive modelling, machine learning, and/or data mining. Generally, predictive modelling may utilize statistics to predict outcomes. Machine learning, while also utilizing statistical techniques, may provide the ability to improve outcome prediction performance without being explicitly programmed to do so. A number of machine learning techniques may be employed to generate and/or modify the layers and/or models describes herein. Those techniques may include, for example, decision tree learning, association rule learning, artificial neural networks (including, in examples, deep learning), inductive logic programming, support vector machines, clustering, Bayesian networks, reinforcement learning, representation learning, similarity and metric learning, sparse dictionary learning, and/or rules-based machine learning.

Information from stored and/or accessible data may be extracted from one or more databases, such as for example the data storage 118, and may be utilized to predict trends and behavior patterns. In examples, the event, otherwise described herein as an outcome, may be an event that will occur in the future, such as whether a member will be hospitalized, a likelihood of a member being diagnosed with diabetes, a likelihood of a member missing a medication prescription fill at a pharmacy, etc. The predictive analytic techniques may be utilized to determine associations and/or relationships between explanatory variables and predicted variables from past occurrences and utilizing these variables to predict the unknown outcome. The predictive analytic techniques may include defining the outcome and data sets used to predict the outcome. Then, data may be collected and/or accessed to be used for analysis, such as from the data storage 118.

Data analysis may include using one or more models, including for example one or more algorithms, to inspect the data with the goal of identifying useful information and arriving at one or more determinations that assist in predicting the outcome of interest. One or more validation operations may be performed, such as using statistical analysis techniques, to validate accuracy of the models, as described more fully herein. Thereafter, predictive modelling may be performed to generate accurate predictive models for future events. Outcome prediction may be deterministic such that the outcome is determined to occur or not occur. Additionally, or alternatively, the outcome prediction may be probabilistic and/or stochastic, such that the outcome is determined to occur to a certain probability and/or confidence.

The model generation techniques described herein may also include at least one of gradient boosting techniques and/or hyperparameter tuning. Gradient boosting may include, for example, producing a prediction model in the form of an ensemble of weak prediction models, which may be decision trees. The prediction model may be built in a stage-wise fashion and may allow optimization of an arbitrary differential loss function. Hyperparameter tuning may include optimization of hyperparameters during a training process. For example, a training data set may be run through the model and the aggregate accuracy of the model may be evaluated. Hyperparameters may be tuned based on the aggregate accuracy.

The training component 124 may be configured to train the one or more models generated by the model generator 122. Training of the models may include, for example, selecting a training population on which to train the model(s). Selection of the training population may include selecting data associated with a group of individuals and/or selecting data associated with a given period of time. Features associated with the data may be identified and/or selected and may be utilized as inputs to the model(s). Training of models may also include and/or be described herein as model fitting. Model fitting may be based at least in part on historical data. For example, once an event is selected, historical data indicating what data and/or data types may be relevant to predicting the event may be utilized. The models may be modified and/or otherwise configured, based at least in part on the historical data, to utilize the data and/or data types relevant to the event to predict the event. Model fitting may include techniques such as linear regression and/or nonlinear regression.

Additionally, or alternatively, while the unfolded records may be independent of each other, an association between records belonging to the same person may be identified and utilized when performing model testing. In these examples, a group of records belonging to a first set of people may be used for training purposes while another group of records belonging to a second set of people may be used for testing purposes. By maintaining an association between records belonging to the same person, records may be split into the two groups without introducing leakage and/or overlap to the testing process.

Additionally, or alternatively, the training component 124 may identify input features that increase the accuracy of the prediction models and other input features that decrease the accuracy of the prediction models or have no or little effect on the prediction models. The prediction models may be refit to utilize the features that increase accuracy while refraining from utilizing the features that decrease accuracy or have no or little effect on accuracy.

The event probability component 126 may be configured to determine an event probability using the model(s) generated by the model generator 122. For example, for a given person associated with the system 108, data associated with the person may be run through the model(s) to determine the probability that a selected event will occur with respect to that person. Using the example provided herein, the probability that a specific person will be hospitalized may be predicted by the system 108. Data associated with the person may be run through the model(s) to determine a probability that the person will be hospitalized, such as during a certain period of time. The model(s) may utilize data available from the data storage 118, for example, to predict the event probability. This process may be repeated for one or more other people associated with the system 108.

The ranking component 128 may be configured to utilize the data generated by the event probability component 126 to provide a ranking. For example, a group of 100 people may be analyzed using the model(s) generated by the model generator 122. The event probability component 126 may determine, for some or all of the people, a probability that the event (e.g., hospitalization) will occur. Those people may be ranked by the ranking component 128 based at least in part on the determined probability.

The recommendation component 130 may be configured to generate recommendations, intervention schedules, incentive program details, and/or to admit or not admit people to a given program based at least in part on the ranking produced by the ranking component 128. By way of example, the recommendation component 130 may generate recommendations associated with information to be provided to individuals that are likely, such as based on the event probability for those individuals being above a threshold event probability threshold, to be hospitalized. The provided information may include a recommendation for those individuals to schedule a health screening with their physician or other medical professional. The provided information may also indicate a healthcare provider that may be suited to assist in such a screening. The provided information may also provide physician-approved actions for lowering the probability of being hospitalized and, in examples, an indication of how much the actions are likely to reduce the risk of hospitalization. The intervention schedules may include treatment programs and/or regimens, which may be physician-approved, to reduce the risk of hospitalization. The admission of a person to a program may include, for example, admission to a complex care program associated with individuals having certain healthcare conditions and/or propensities. It should be understood that while the examples of recommendations, schedules, and admission decisions are provided herein, they are provided by way of illustration unless otherwise noted and/or claimed. This disclosure includes the identification, determination, and/or generation of recommendations of any and all types, particularly those relevant to and/or associated with the event in question and/or the data being analyzed, and/or the model(s) being generated.

The validation component 132 may be configured to validate the one or more models using one or more validation techniques. For example, an area-under-the-resource-operating-characteristic-curve measurement may be utilized to gauge the accuracy of the model generated utilizing the unfolded data. In examples, the measurement may be at least 0.75, at least 0.76, at least 0.77, at least 0.78, at least 0.79, at least 0.80, at least 0.81, at least 0.82, at least 0.83, at least 0.84, at least 0.85, at least 0.86, at least 0.87, at least 0.88, at least 0.89, or at least 0.90, indicating a high degree of accuracy. Additionally, or alternatively, precision-recall characteristic measurements may be utilized to determine precision of the prediction models.

As used herein, a processor, such as processor(s) 112, may include multiple processors and/or a processor having multiple cores. Further, the processors may comprise one or more cores of different types. For example, the processors may include application processor units, graphic processing units, and so forth. In one implementation, the processor may comprise a microcontroller and/or a microprocessor. The processor(s) 112 may include a graphics processing unit (GPU), a microprocessor, a digital signal processor or other processing units or components known in the art. Alternatively, or in addition, the functionally described herein can be performed, at least in part, by one or more hardware logic components. For example, and without limitation, illustrative types of hardware logic components that can be used include field-programmable gate arrays (FPGAs), application-specific integrated circuits (ASICs), application-specific standard products (ASSPs), system-on-a-chip systems (SOCs), complex programmable logic devices (CPLDs), etc. Additionally, each of the processor(s) 112 may possess its own local memory, which also may store program components, program data, and/or one or more operating systems.

The memory 116 may include volatile and nonvolatile memory, removable and non-removable media implemented in any method or technology for storage of information, such as computer-readable instructions, data structures, program component, or other data. Such memory 116 includes, but is not limited to, RAM, ROM, EEPROM, flash memory or other memory technology, CD-ROM, digital versatile disks (DVD) or other optical storage, magnetic cassettes, magnetic tape, magnetic disk storage or other magnetic storage devices, RAID storage systems, or any other medium which can be used to store the desired information and which can be accessed by a computing device. The memory 116 may be implemented as computer-readable storage media ("CRSM"), which may be any available physical media accessible by the processor(s) 112 to execute instructions stored on the memory 116. In one basic implementation, CRSM may include random access memory ("RAM") and Flash memory. In other implementations, CRSM may include, but is not limited to, read-only memory ("ROM"), electrically erasable programmable read-only memory ("EEPROM"), or any other tangible medium which can be used to store the desired information and which can be accessed by the processor(s).

Further, functional components may be stored in the respective memories, or the same functionality may alternatively be implemented in hardware, firmware, application specific integrated circuits, field programmable gate arrays, or as a system on a chip (SoC). In addition, while not illustrated, each respective memory, such as memory 116, discussed herein may include at least one operating system (OS) component that is configured to manage hardware resource devices such as the network interface(s), the I/O devices of the respective apparatuses, and so forth, and provide various services to applications or components executing on the processors. Such OS component may implement a variant of the FreeBSD® operating system as promulgated by the FreeBSD® Project; other UNIX® or UNIX®-like variants; a variation of the Linux® operating system as promulgated by Linus Torvalds; the FireOS® operating system from Amazon.com Inc. of Seattle, Wash., USA; the Windows® operating system from Microsoft® Corporation of Redmond, Wash., USA; LynxOS® as promulgated by Lynx Software Technologies, Inc. of San Jose, Calif.; Operating System Embedded (Enea® OSE) as promulgated by ENEA AB of Sweden; and so forth.

The network interface(s) 114 may enable communications between the components and/or devices shown in environment 100 and/or with one or more other remote systems, as well as other networked devices. Such network interface(s) 114 may include one or more network interface controllers (NICs) or other types of transceiver devices to send and receive communications over the network 110.

For instance, each of the network interface(s) 114 may include a personal area network (PAN) component to enable communications over one or more short-range wireless communication channels. For instance, the PAN component may enable communications compliant with at least one of the following standards IEEE 802.15.4 (ZigBee), IEEE 802.15.1 (Bluetooth), IEEE 802.11 (WiFi), or any other PAN communication protocol. Furthermore, each of the network interface(s) 114 may include a wide area network (WAN) component to enable communication over a wide area network.

Figure 2:
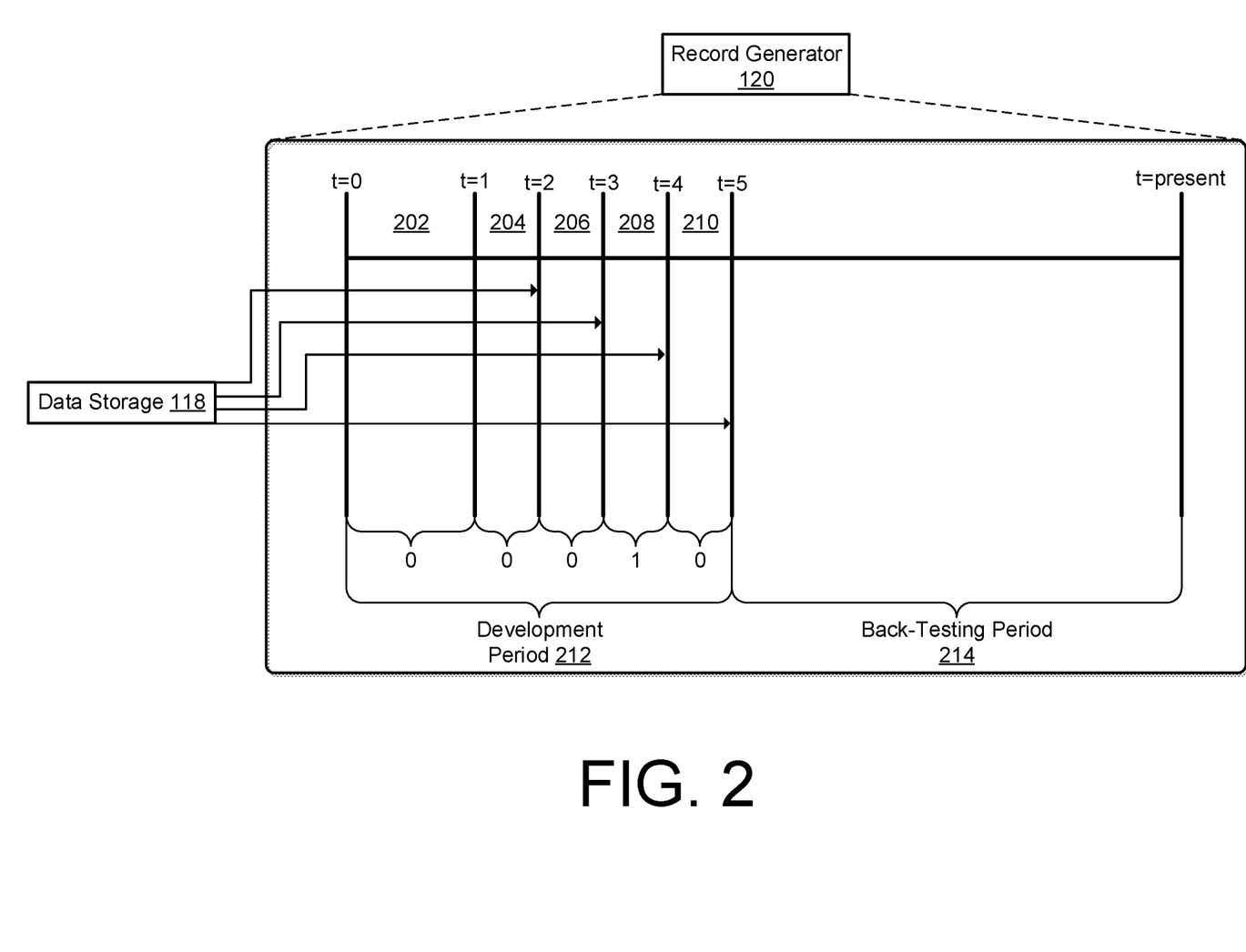
FIG. 2 illustrates a conceptual diagram of components and/or operations associated with a record generator for data folding and unfolding.

FIG. 2 illustrates a conceptual diagram of components and/or operations associated with a record generator 120 for data unfolding. The record generator 120 may utilize data from one or more sources, such as the data storage 118 to evaluate data folds and generate records, such as to increase the quantity and/or quality of data available to the data storage 118.

The record generator 120 may be configured to perform the folding and/or unfolding processes described herein. For example, the record generator 120 may be configured to identify, determine, and/or receive an indication of a time interval 202-210 at which to generate records. Keeping with the example used herein, the time interval 202-210 may be, for example, 28 days. Other time intervals may be utilized. The record generator 120 may also be configured to identify, determine, and/or receive an indication of a period of time 212 during which to generate records. For example, a particular time frame 212 may be utilized to generate the records and/or an amount of time from a certain date may be utilized. For example, the record generator 120 may identify a one-year period of time during which to generate records. Alternatively, the record generator 120 may identify a date, such as Jan. 1, 2017, from which to start record generation either moving forward or backward in time. The record generator 120 may be further configured to identify, determine, and/or receive an indication of the data sources from which to utilize data. For example, the record generator 120 may identify, determine, and/or receive an indication that the data storage 118 is to be utilized for receiving data from.

The record generator 120 may be further configured to identify, determine, and/or receive an indication of an event to analyze with respect to the data. For example, the record generator 120 may identify, determine, and/or receive an indication that an event of interest is hospitalization. The record generator 120 may then determine, for each time interval during the identified time period, whether the event occurred. For example, the system may determine that for a first time interval 202, illustrated as from $t=0$ to $t=1$, a particular person was not hospitalized. This is illustrated as a "0" with respect to the first time interval 202. The system may determine that for a second time interval 204, illustrated as from $t=1$ to $t=2$, the person was not hospitalized. The system may determine that for a third time interval 206, illustrated as from $t=2$ to $t=3$, the person was not hospitalized. The system may determine that for a fourth time interval 208, illustrated as from $t=3$ to $t=4$, the person was hospitalized. This is illustrated as a "1" with respect to the fourth time interval 208. The system may also determine that for a fifth time interval 210, illustrated as from $t=4$ to $t=5$, the person was not hospitalized. This process may be performed for all or some of the people on which data is available to the system. In examples, the system may identify, determine, and/or receive an indication of the people, the number of people, and/or categories of people on which to perform the processes described herein.

In the example used herein, the folding of data as described above may result in the generation of five records for the person in question. For the example person illustrated herein, the first record may include data associated with the person (e.g., blood pressure, age, weight, etc.) for the first time interval 202 and an indication that the person was not hospitalized. The second record may include data associated with the person for the second time interval 204 and an indication that the person was not hospitalized. The third record may include data associated with the person for the third time interval 206 and an indication that the person was not hospitalized. The fourth record may include data associated with the person for the fourth time interval 208 and an indication that the person was hospitalized. The fifth record may include data associated with the person for the fifth time interval 210 and an indication that the person was not hospitalized.

By folding data as described above and elsewhere herein, multiple records may be generated for each person associated with the system and/or each person selected for data folding. In the example provided above, the original data record associated with the example person, which indicates that the person was at some point hospitalized, may be utilized to generate five independent records with data and their own indications of hospitalization events. The records may be unfolded, or otherwise separated from each other as independent records for use by the system as described herein. Extrapolating from the example provided herein, the system may have access to data for 100,000 people, which amounts to 100,000 records with one record for each person. Utilizing the data folding and unfolding techniques described herein, such as using 5 time intervals during the folding processes, 500,000 records may be generated and then utilized by the system.

Additionally, or alternatively, a testing period 214 may be identified, determined, and/or indicated. As illustrated with respect to FIG. 2, the testing period 214 may be from t=5 to t=present, for example. The predictive model(s), as described more fully herein with respect to FIG. 1, may be generated based on the data and/or records available during the first period 212, which may be described as a development period during which the model(s) are developed. By way of example, a portion of the records associated with the first period 212 may be utilized to train the predictive model(s). Thereafter, the model(s) may be further trained and/or tested during a second period 214, which may be described as a back-testing period. During the back-testing period, data not associated with data utilized to develop the model(s) may be utilized to train and/or test the model(s). It should also be noted that while the back-testing period 214 is depicted as utilizing data from t=5 to t=present, the utilized data may include data from t=5 to a time that is less than t=present.

Figure 3:
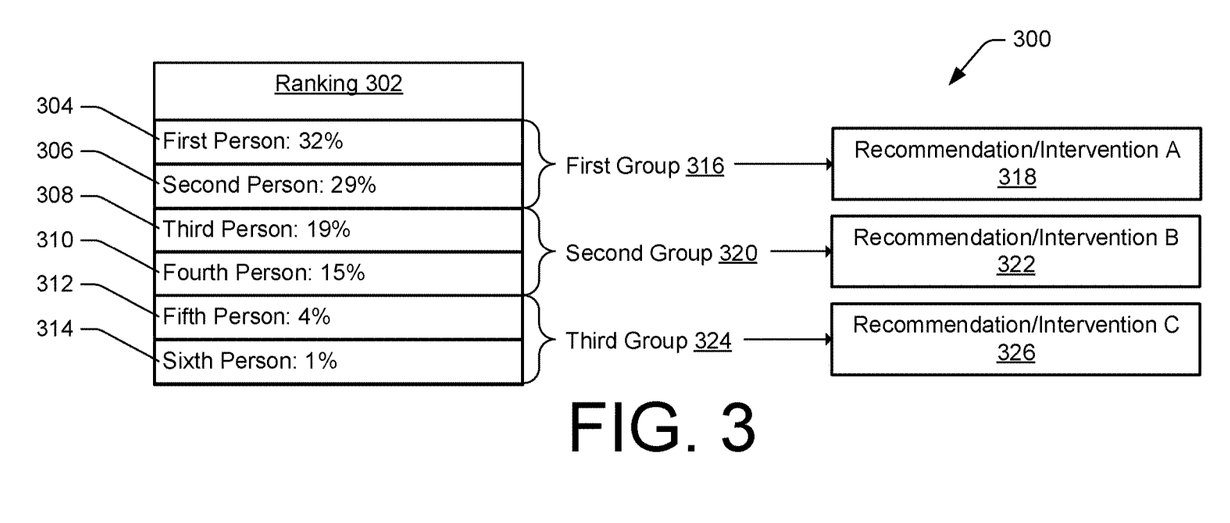
FIG. 3 illustrates a conceptual diagram of example ranked data entries and uses of the same.

FIG. 3 illustrates a conceptual diagram of example ranked data entries and uses of the same. For example, the environment 300 may include a ranking 302. The ranking 302 may include one or more entity entries 304-314. The entity entries 304-314 may correspond to people, entities, objects, and/or other identifiers of entities associated with a system such as that disclosed herein. Using FIG. 3 as an example, the entity entries 304-314 may correspond to people whose data has been acquired by a system. The folding and unfolding techniques described herein may be performed on the data associated with the people, and one or more prediction models may be identified and/or generated to predict a likelihood that an event will occur. Sticking with the example provided above, the event may be hospitalization. As shown in FIG. 3, the likelihood that the people associated with the six entity entries 304-314 will be hospitalized in a given period of time is provided by way of percentages. It should be understood that the likelihood of an event occurring may be expressed in terms other than, or in addition to, percentages. For example, the likelihood may be presented as a scale, a coefficient, and/or a narrative.

As shown in FIG. 3, the first entity entry 304 corresponds to First Person, and the model(s) described herein have been utilized to determine that First Person has a 32% likelihood of being hospitalized within a given period of time. The second entity entry 306 corresponds to Second Person, and the model(s) described herein have been utilized to determine that Second Person has a 29% likelihood of being hospitalized within a given period of time. The third entity entry 308 corresponds to Third Person, and the model(s) described herein have been utilized to determine that Third Person has a 19% likelihood of being hospitalized within a given period of time. The fourth entity entry 310 corresponds to Fourth Person, and the model(s) described herein have been utilized to determine that Fourth Person has a 15% likelihood of being hospitalized within a given period of time. The fifth entity entry 312 corresponds to Fifth Person, and the model(s) described herein have been utilized to determine that Fifth Person has a 4% likelihood of being hospitalized within a given period of time. The sixth entity entry 314 corresponds to Sixth Person, and the model(s) described herein have been utilized to determine that Sixth Person has a 1% likelihood of being hospitalized within a given period of time. It should be understood that while FIG. 3 depicts six entity entries 304-314, the ranking 302 may include one, two, three, four, five, six, or more than six entity entries 304-314.

Once the entities are ranked, such as via the ranking 302, the entities may be grouped. For example, one or more thresholds may be identified, determined, and/or generated based at least in part on information such as historical information, budgetary information, system resources, policies, procedures, and/or government statutes and/or regulations. The thresholds may be informed by the action to be taken in light of the event being predicted. For example, when the event being predicted is hospitalization, the system may be configured to attempt to minimize hospitalizations, and in doing so, may be programmed to indicate which group(s) of people are most at risk for being hospitalized so that interventions may be put in place to mitigate such risk. For example, a first threshold may be set at 20% probability that a person will be hospitalized. Entities that are associated with a 20% or higher hospitalization probability may be associated with a first group 316, which may correspond to high-risk individuals. Entities that are associated with between a 10% hospitalization threshold and a 20% hospitalization threshold may be associated with a second group 320, which may correspond to medium-risk individuals. Entities that are associated with less than a 10% hospitalization threshold may be associated with a third group 324 which may correspond to low-risk individuals. It should be understood that while three groups are depicted in FIG. 3, the groupings may include one, two, three, or more than three groupings. It should also be understood that while three thresholds and/or threshold ranges are provided herein, the groupings may be based on one, two, three, or more than three thresholds and/or threshold ranges.

Some or all of the groupings may be associated with a given recommendation and/or intervention. For example, a recommendation and/or intervention may be identified, determined, and/or generated based at least in part on a particular grouping. Using FIG. 3 as an example, Recommendation and/or Intervention A 318 may be associated with the first group of individuals 316. Given that the first group 316 corresponds to a high-risk group, the Recommendation and/or Intervention A 318 may correspond to a recommendation that is more severe and/or dedicates a large amount of resources, for example, than other recommendations. In the instance where the event is hospitalization, the recommendation may include a dietary recommendation, a physical fitness recommendation, a recommendation to schedule a checkup with a healthcare provider (as well as, in examples, information associated with one or more healthcare providers), etc. The intervention may include an intervention schedule such as changes to scheduled healthcare checkups, changes to medications, changes to delivery of dietary products and/or foods, etc. Continuing with the example above, Recommendation and/or Intervention B 322 may be associated with the second group of individuals 320. Given that the second group 320 corresponds to a medium-risk group, the Recommendation and/or Intervention B 322 may correspond to a recommendation that is less severe and/or dedicates less resources, for example, than Recommendation and/or Intervention A 318. Recommendation and/or Intervention C 326 may be associated with the third group of individuals 324. Given that the third group 324 corresponds to a low-risk group, the Recommendation and/or Intervention C 326 may correspond to a recommendation that is less severe and/or dedicates less resources, for example, than Recommendation and/or Intervention B 322.

Figure 4:
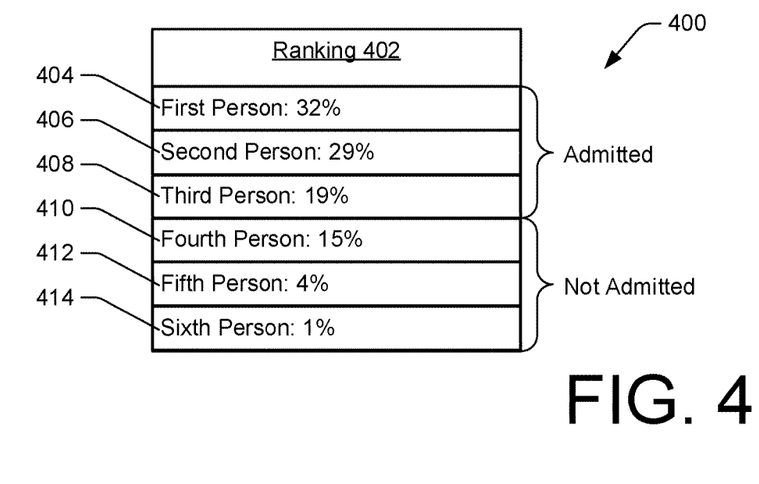
FIG. 4 illustrates a conceptual diagram of example ranked data entries and further uses of the same.

FIG. 4 illustrates a conceptual diagram of example ranked data entries and further uses of the same. For example, the environment 400 may include a ranking 402. The ranking 402 may include one or more entity entries 404-414. The entity entries 404-414 may correspond to people, entities, objects, and/or other identifiers of entities associated with a system, such as described with respect to FIG. 3. As shown in FIG. 4, the likelihood that people associated with the six entity entries 404-414 will be hospitalized in a given period of time is provided by way of percentages. It should be understood that the likelihood of an event occurring may be expressed in terms other than, or in addition to, percentages. For example, the likelihood may be presented as a scale, a coefficient, and/or a narrative.

As shown in FIG. 4, the first entity entry 404 corresponds to First Person, and the model(s) described herein have been utilized to determine that First Person has a 32% likelihood of being hospitalized within a given period of time. The second entity entry 406 corresponds to Second Person, and the model(s) described herein have been utilized to determine that Second Person has a 29% likelihood of being hospitalized within a given period of time. The third entity entry 408 corresponds to Third Person, and the model(s) described herein have been utilized to determine that Third Person has a 19% likelihood of being hospitalized within a given period of time. The fourth entity entry 410 corresponds to Fourth Person, and the model(s) described herein have been utilized to determine that Fourth Person has a 15% likelihood of being hospitalized within a given period of time. The fifth entity entry 412 corresponds to Fifth Person, and the model(s) described herein have been utilized to determine that Fifth Person has a 4% likelihood of being hospitalized within a given period of time. The sixth entity entry 414 corresponds to Sixth Person, and the model(s) described herein have been utilized to determine that Sixth Person has a 1% likelihood of being hospitalized within a given period of time. It should be understood that while FIG. 4 depicts six entity entries 404-414, the ranking 402 may include one, two, three, four, five, six, or more than six entity entries 404-414.

Once the entities are ranked, such as via the ranking 402, the entities may be grouped. As shown in FIG. 4, the rankings 402 may be utilized to group individuals between two or more categories, here depicted as "admitted" or "not admitted." As such, the ranking 402 may be utilized to identify and/or determine which people will be admitted to a program and which people will not be admitted to the program. An admittance threshold may be identified, determined, and/or generated and people with event probabilities meeting or exceeding the admittance threshold may be admitted, while people with event probabilities not meeting or exceeding the admittance threshold may not be admitted.

Figure 5:
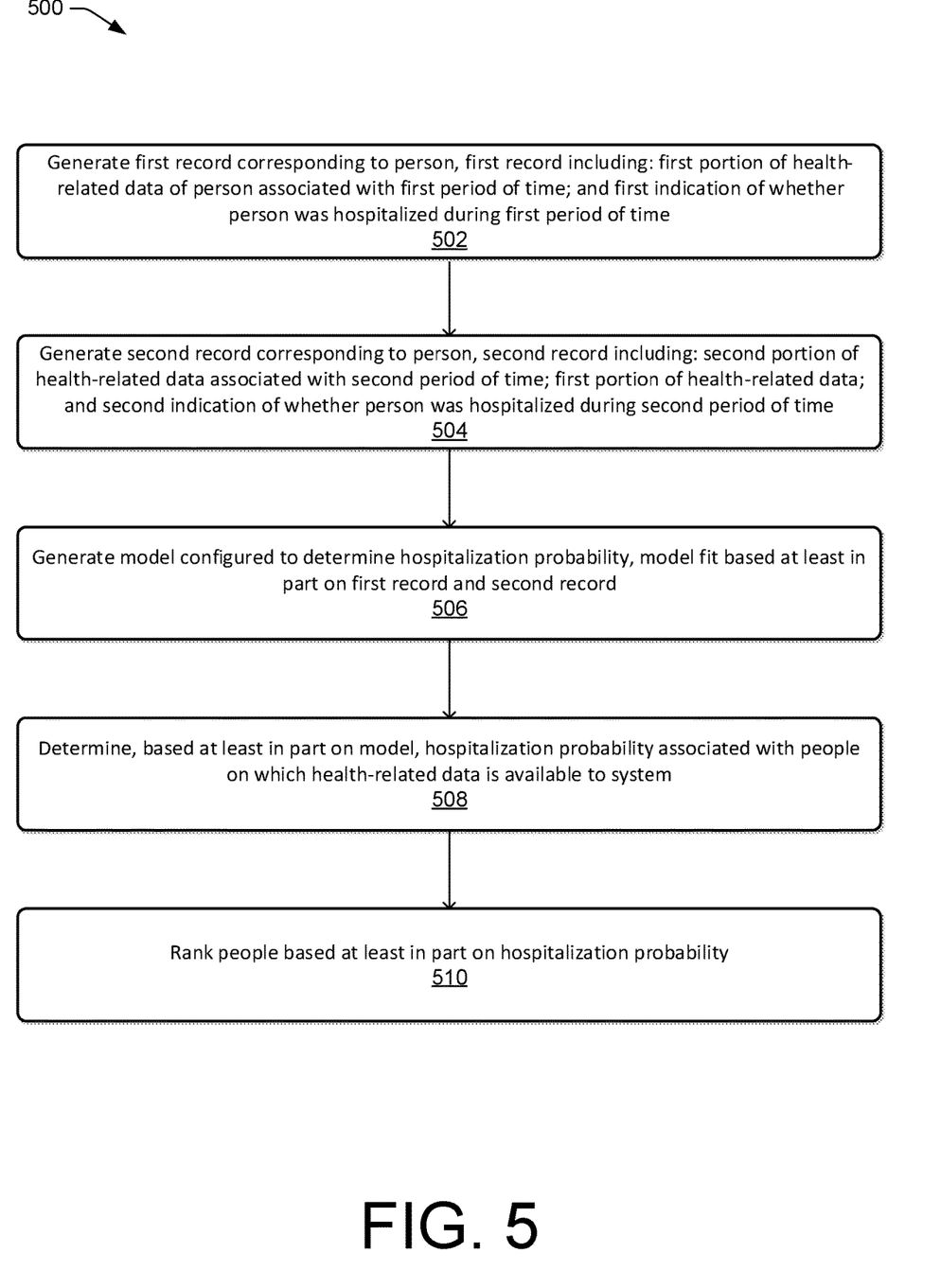
FIG. 5 illustrates a flow diagram of an example process for data folding and unfolding.
Figure 6:
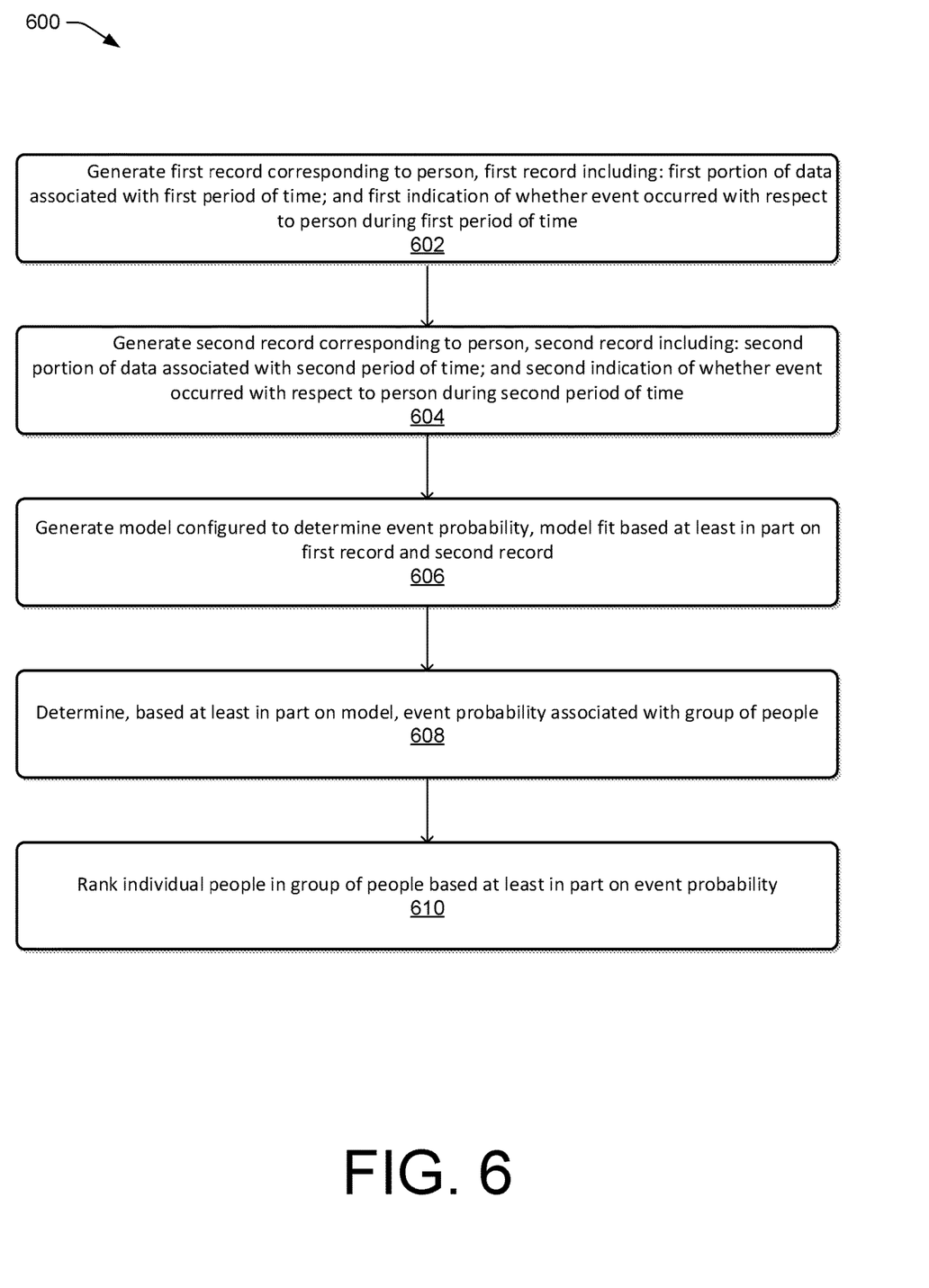
FIG. 6 illustrates a flow diagram of another example process for data folding and unfolding.

FIGS. 5 and 6 illustrate various processes for data folding and unfolding. The processes described herein are illustrated as collections of blocks in logical flow diagrams, which represent a sequence of operations, some or all of which may be implemented in hardware, software or a combination thereof. In the context of software, the blocks may represent computer-executable instructions stored on one or more computer-readable media that, when executed by one or more processors, program the processors to perform the recited operations. Generally, computer-executable instructions include routines, programs, objects, components, data structures and the like that perform particular functions or implement particular data types. The order in which the blocks are described should not be construed as a limitation, unless specifically noted. Any number of the described blocks may be combined in any order and/or in parallel to implement the process, or alternative processes, and not all of the blocks need be executed. For discussion purposes, the processes are described with reference to the environments, architectures and systems described in the examples herein, such as, for example those described with respect to FIGS. 1-4, although the processes may be implemented in a wide variety of other environments, architectures and systems.

FIG. 5 illustrates a flow diagram of an example process 500 for data folding and unfolding. The order in which the operations or steps are described is not intended to be construed as a limitation, and any number of the described operations may be combined in any order and/or in parallel to implement process 500.

At block 502, the process 500 may include generating a first record corresponding to a person, the first record including: a first portion of health-related data of the person associated with a first period of time; and a first indication of whether the person was hospitalized during the first period of time. For example, a record generator may be configured to perform folding and/or unfolding processes, as described herein. For example, the record generator may be configured to identify, determine, and/or receive an indication of a time interval at which to generate records. The record generator may also be configured to identify, determine, and/or receive an indication of a period of time during which to generate records. For example, a particular time frame may be utilized to generate the records and/or an amount of time from a certain date may be utilized.

The record generator may be further configured to identify, determine, and/or receive an indication of the data sources from which to utilize data. For example, the record generator may identify, determine, and/or receive an indication that a data storage component is to be utilized for receiving data from. Additionally, or alternatively, the record generator may identify, determine, and/or receive an indication that one or more other data sources are to be utilized in addition to or alternatively to the data storage.

The record generator may be further configured to identify, determine, and/or receive an indication of an event to analyze with respect to the data. For example, the record generator may identify, determine, and/or receive an indication that an event of interest is hospitalization. The record generator may then determine, for each time interval during the identified time period, whether the event occurred. For example, the system may determine that for a first time interval the person was not hospitalized, and for a second time interval the person was hospitalized. This process may be performed for all or some of the people on which data is available to the system. In examples, the system may identify, determine, and/or receive an indication of the people, the number of people, and/or categories of people on which to perform the processes described herein.

In the example used herein, the folding of data as described above may result in the generation of two records for each person. For the example person illustrated herein, the first record may include data associated with the person (e.g., blood pressure, age, weight, etc.) for the first period of time and an indication that the person was not hospitalized. The second record may include data associated with the person for the second period of time and an indication that the person was hospitalized.

By folding data as described above and elsewhere herein, multiple records may be generated for each person associated with the system and/or each person selected for data folding. In the example provided above, the original data record associated with the example person, which indicates that the person was at some point hospitalized, may be utilized to generate two independent records with data and their own indications of hospitalization events. The records may be unfolded, or otherwise separated from each other as independent records for use by the system as described herein.

At block 504, the process 500 may include generating a second record corresponding to the person, the second record including: a second portion of the health-related data associated with a second period of time; and a second indication of whether the person was hospitalized during the second period of time. Generation of the second record may be performed in the same or a similar manner as generation of the first record, described with respect to block 502.

At block 506, the process 500 may include generating a model configured to determine a hospitalization probability, the model fit based at least in part on the first record and the second record. For example, a model generator may be configured to generate one or more models based at least in part on the records generated by the record generator and/or other data available to the system. The more robust data set generated by the folding and unfolding techniques described herein may increase the data sampling available to the models, which may allow those models to be trained and/or fit more accurately. The models may be generated utilizing, for example, one or more machine learning techniques where features associated with the health-related data are inputs to the model. The models may be utilized to determine a probability of an outcome occurring, such as for people associated with the system. These models may be described herein as predictive models and/or predictive layers. A predictive model may include one or more models that utilize predictive analytics to predict one or more outcomes. Predictive analytic techniques may include, for example, predictive modelling, machine learning, and/or data mining, as described more fully above.

Information from stored and/or accessible data may be extracted from one or more databases and may be utilized to predict trends and behavior patterns. In examples, the event, otherwise described herein as an outcome, may be an event that will occur in the future, such as whether a member will be hospitalized, a likelihood of a member being diagnosed with diabetes, a likelihood of a member missing a medication prescription fill at a pharmacy, etc. The predictive analytic techniques may be utilized to determine associations and/or relationships between explanatory variables and predicted variables from past occurrences and utilizing these variables to predict the unknown outcome. The predictive analytic techniques may include defining the outcome and data sets used to predict the outcome. Then, data may be collected and/or accessed to be used for analysis.

Data analysis may include using one or more models, including for example one or more algorithms, to inspect the data with the goal of identifying useful information and arriving at one or more determinations that assist in predicting the outcome of interest. One or more validation operations may be performed, such as using statistical analysis techniques, to validate accuracy of the models, as described more fully herein. Thereafter predictive modelling may be performed to generate accurate predictive models for future events. Outcome prediction may be deterministic such that the outcome is determined to occur or not occur. Additionally, or alternatively, the outcome prediction may be probabilistic and/or stochastic, such that the outcome is determined to occur to a certain probability and/or confidence.

The model generation techniques described herein may also include at least one of gradient boosting techniques and/or hyperparameter tuning. Gradient boosting may include, for example, producing a prediction model in the form of an ensemble of weak prediction models, which may be decision trees. The prediction model may be built in a stage-wise fashion and may allow optimization of an arbitrary differential loss function. Hyperparameter tuning may include optimization of hyperparameters during a training process. For example, a training data set may be run through the model and the aggregate accuracy of the model may be evaluated. Hyperparameters may be tuned based on the aggregate accuracy.

A validation component may be configured to validate the one or more models using one or more validation techniques. For example, an area-under-the-resource-operating-characteristic-curve measurement may be utilized to gauge the accuracy of the model generated utilizing the unfolded data. In examples, the measurement may be at least 0.75, at least 0.76, at least 0.77, at least 0.78, at least 0.79, at least 0.80, at least 0.81, at least 0.82, at least 0.83, at least 0.84, at least 0.85, at least 0.86, at least 0.87, at least 0.88, at least 0.89, or at least 0.90, indicating a high degree of accuracy. Additionally, or alternatively, precision-recall characteristic measurements may be utilized to determine precision of the prediction models.

At block 508, the process 500 may include determining, based at least in part on the model, the hospitalization probability associated with people on which health-related data is available to the system. For example, an event probability component may be configured to determine an event probability using the model(s) generated by the model generator. For example, for a given person associated with the system, data associated with the person may be run through the model(s) to determine the probability that a selected event will occur with respect to that person. Using the example provided herein, the probability that a specific person will be hospitalized may be predicted by the system. Data associated with the person may be run through the model(s) to determine a probability that the person will be hospitalized, such as during a certain period of time. The model(s) may utilize data available from the data storage, for example, to predict the event probability. This process may be repeated for one or more other people associated with the system.

At block 510, the process 500 may include ranking the people based at least in part on the hospitalization probability. For example, the ranking component may be configured to utilize the data generated by the event probability component to provide a ranking. For example, a group of 100 people may be analyzed using the model(s) generated by the model generator. The event probability component may determine, for some or all of the people, a probability that the event (e.g., hospitalization) will occur. Those people may be ranked by the ranking component based at least in part on the determined probability.

The process 500 may additionally, or alternatively, include identifying a hospitalization probability threshold and identifying a portion of the people with hospitalization probabilities at or above the hospitalization probability threshold. The process 500 may also include generating an intervention recommendation for the portion of the people based at least in part on the hospitalization probabilities being at or above the hospitalization probability threshold.

The process 500 may additionally, or alternatively, include determining a difference between (1) the hospitalization probability determined by the model with respect to a portion of the people and (2) hospitalization events occurring with respect to the portion of the people. The process 500 may also include generating a modified model based at least in part on the difference.

FIG. 6 illustrates a flow diagram of an example process 600 for data folding and unfolding. The order in which the operations or steps are described is not intended to be construed as a limitation, and any number of the described operations may be combined in any order and/or in parallel to implement process 600.

At block 602, the process 600 may include generating a first record corresponding to a person, the first record including: a first portion of data associated with a first period of time; and a first indication of whether an event occurred with respect to the person during the first period of time. For example, a record generator may be configured to perform folding and/or unfolding processes, as described herein. For example, the record generator may be configured to identify, determine, and/or receive an indication of a time interval at which to generate records. The record generator may also be configured to identify, determine, and/or receive an indication of a period of time during which to generate records. For example, a particular time frame may be utilized to generate the records and/or an amount of time from a certain date may be utilized.

The record generator may be further configured to identify, determine, and/or receive an indication of the data sources from which to utilize data. For example, the record generator may identify, determine, and/or receive an indication that a data storage component is to be utilized for receiving data from. Additionally, or alternatively, the record generator may identify, determine, and/or receive an indication that one or more other data sources are to be utilized in addition to or alternatively to the data storage.

The record generator may be further configured to identify, determine, and/or receive an indication of an event to analyze with respect to the data. For example, the record generator may identify, determine, and/or receive an indication that an event of interest, such as hospitalization. The record generator may then determine, for each time interval during the identified time period, whether the event occurred. For example, the system may determine that for a first time interval the person was not hospitalized, and for a second time interval the person was hospitalized. This process may be performed for all or some of the people on which data is available to the system. In examples, the system may identify, determine, and/or receive an indication of the people, the number of people, and/or categories of people on which to perform the processes described herein.

In the example used herein, the folding of data as described above may result in the generation of two records for each person. For the example person illustrated herein, the first record may include data associated with the person (e.g., blood pressure, age, weight, etc.) for the first period of time and an indication that the person was not hospitalized. The second record may include data associated with the person for the second period of time and an indication that the person was hospitalized.

By folding data as described above and elsewhere herein, multiple records may be generated for each person associated with the system and/or each person selected for data folding. In the example provided above, the original data record associated with the example person, which indicates that the person was at some point hospitalized, may be utilized to generate two independent records with data and their own indications of hospitalization events. The records may be unfolded, or otherwise separated from each other as independent records for use by the system as described herein.

At block 604, the process 600 may include generating a second record corresponding to the person, the second record including: a second portion of the data associated with a second period of time; and a second indication of whether the event occurred with respect to the person during the second period of time. Generation of the second record may be performed in the same or a similar manner as generation of the first record, described with respect to block 602.

At block 606, the process 600 may include generating a model configured to determine an event probability, the model fit based at least in part on the first record and the second record. For example, a model generator may be configured to generate one or more models based at least in part on the records generated by the record generator and/or other data available to the system. The more robust data set generated by the folding and unfolding techniques described herein may increase the data sampling available to the models, which may allow those models to be trained and/or fit more accurately. The models may be generated utilizing, for example, one or more machine learning techniques where features associated with the health-related data are inputs to the model. The models may be utilized to determine a probability of an outcome occurring, such as for people associated with the system. These models may be described herein as predictive models and/or predictive layers. A predictive model may include one or more models that utilize predictive analytics to predict one or more outcomes. Predictive analytic techniques may include, for example, predictive modelling, machine learning, and/or data mining, as described more fully above.

Information from stored and/or accessible data may be extracted from one or more databases and may be utilized to predict trends and behavior patterns. In examples, the event, otherwise described herein as an outcome, may be an event that will occur in the future, such as whether a member will be hospitalized, a likelihood of a member being diagnosed with diabetes, a likelihood of a member missing a medication prescription fill at a pharmacy, etc. The predictive analytic techniques may be utilized to determine associations and/or relationships between explanatory variables and predicted variables from past occurrences and utilizing these variables to predict the unknown outcome. The predictive analytic techniques may include defining the outcome and data sets used to predict the outcome. Then, data may be collected and/or accessed to be used for analysis.

Data analysis may include using one or more models, including for example one or more algorithms, to inspect the data with the goal of identifying useful information and arriving at one or more determinations that assist in predicting the outcome of interest. One or more validation operations may be performed, such as using statistical analysis techniques, to validate accuracy of the models, as described more fully herein. Thereafter predictive modelling may be performed to generate accurate predictive models for future events. Outcome prediction may be deterministic such that the outcome is determined to occur or not occur. Additionally, or alternatively, the outcome prediction may be probabilistic and/or stochastic, such that the outcome is determined to occur to a certain probability and/or confidence.

The model generation techniques described herein may also include at least one of gradient boosting techniques and/or hyperparameter tuning. Gradient boosting may include, for example, producing a prediction model in the form of an ensemble of weak prediction models, which may be decision trees. The prediction model may be built in a stage-wise fashion and may allow optimization of an arbitrary differential loss function. Hyperparameter tuning may include optimization of hyperparameters during a training process. For example, a training data set may be run through the model and the aggregate accuracy of the model may be evaluated. Hyperparameters may be tuned based on the aggregate accuracy.

A validation component may be configured to validate the one or more models using one or more validation techniques. For example, an area-under-the-resource-operating-characteristic-curve measurement may be utilized to gauge the accuracy of the model generated utilizing the unfolded data. In examples, the measurement may be at least 0.75, at least 0.76, at least 0.77, at least 0.78, at least 0.79, at least 0.80, at least 0.81, at least 0.82, at least 0.83, at least 0.84, at least 0.85, at least 0.86, at least 0.87, at least 0.88, at least 0.89, or at least 0.90, indicating a high degree of accuracy. Additionally, or alternatively, precision-recall characteristic measurements may be utilized to determine precision of the prediction models.

At block 608, the process 600 may include determining, based at least in part on the model, the event probability associated with a group of people. For example, an event probability component may be configured to determine an event probability using the model(s) generated by the model generator. For example, for a given person associated with the system, data associated with the person may be run through the model(s) to determine the probability that a selected event will occur with respect to that person. Using the example provided herein, the probability that a specific person will be hospitalized may be predicted by the system. Data associated with the person may be run through the model(s) to determine a probability that the person will be hospitalized, such as during a certain period of time. The model(s) may utilize data available from the data storage, for example, to predict the event probability. This process may be repeated for one or more other people associated with the system.

At block 610, the process 600 may include ranking individual people in the group of people based at least in part on the event probability. For example, the ranking component may be configured to utilize the data generated by the event probability component to provide a ranking. For example, a group of 100 people may be analyzed using the model(s) generated by the model generator. The event probability component may determine, for some or all of the people, a probability that the event (e.g., hospitalization) will occur. Those people may be ranked by the ranking component based at least in part on the determined probability.

The process 600 may additionally, or alternatively, include identifying an event probability threshold and identifying a portion of the group of people with event probabilities at or above the event probability threshold. The process 600 may also include generating a recommendation for the portion of the group of people based at least in part on the event probabilities being at or above the event probability threshold.

The process 600 may additionally, or alternatively, include determining a difference between (1) the event probability determined by the model with respect to a portion of the group of people and (2) event occurrences with respect to the portion of the group of people. The process 600 may also include generating a modified model based at least in part on the difference.

The process 600 may additionally, or alternatively, include generating the model based at least in part on identifying a first group of input features that, when utilized by the model, increase an accuracy of the model and identifying a second group of the input features that, when utilized by the model, decrease the accuracy of the model or maintain the accuracy of the model. The process 600 may also include refitting the model to utilize the first group of the input features and refrain from utilizing the second group of the input features.

The process 600 may additionally, or alternatively, include identifying an event probability threshold and identifying a portion of the group of people with event probabilities at or above the event probability threshold. The process 600 may also include causing the portion of the group of people to be accepted into a program based at least in part on the event probabilities being at or above the event probability threshold.

While the foregoing invention is described with respect to the specific examples, it is to be understood that the scope of the invention is not limited to these specific examples. Since other modifications and changes varied to fit particular operating requirements and environments will be apparent to those skilled in the art, the invention is not considered limited to the example chosen for purposes of disclosure, and covers all changes and modifications which do not constitute departures from the true spirit and scope of this invention.

Although the application describes embodiments having specific structural features and/or methodological acts, it is to be understood that the claims are not necessarily limited to the specific features or acts described. Rather, the specific features and acts are merely illustrative some embodiments that fall within the scope of the claims of the application.

What is claimed is:

1. A system comprising:
one or more processors; and
computer-readable media storing first computer-executable instructions that, when executed by the one or more processors, cause the one or more processors to perform operations comprising:
receiving, from a database and at a first time, health-related data of a person;
determining a time interval for splitting the health-related data into multiple records, wherein each of the multiple records corresponds to a second time that occurred before the first time;
generating, utilizing for a first instance of the time interval, a first record representing:

a first portion of the health-related data attributable to the first instance of the time interval; and a first indication of whether the person was hospitalized during the first instance of the time interval;

generating, utilizing a second instance of the time interval, a second record representing:

a second portion of the health-related data attributable to the second instance of the time interval; and a second indication of whether the person was hospitalized during the second instance of the time interval;

dissociating the first record from the second record such that the first record and the second record are indicated as being independent of each other;

storing the first record and the second record such that the first record and the second record are indicated as being dissociated;

generating a machine-learning model configured to determine a hospitalization probability;

generating a training dataset configured to train the machine-learning model, the training dataset including the dissociation of the first record and the second record, the health-related data, the first instance of the time interval, the second first instance of the time interval, the first record and, the second record;

training the machine-learning model utilizing the training dataset to identify trends between the dissociation of the first record and the second record, the health related data, the first instance of the time interval, the second first instance of the time interval, the first record, and the second record to determine if a hospitalization probability of a patient is improved;

determining, based at least in part on the trained machine-learning model, the hospitalization probability associated with people on which health-related data is available to the system; and ranking the people based at least in part on the hospitalization probability and utilizing the trained machine-learning model.

2. The system of claim 1, the operations further comprising:

identifying a hospitalization probability threshold;

identifying a portion of the people with hospitalization probabilities at or above the hospitalization probability threshold; and generating an intervention recommendation for the portion of the people based at least in part on the hospitalization probabilities being at or above the hospitalization probability threshold.

3. The system of claim 1, wherein generating the machine-learning model comprises generating the machine-learning model based at least in part on features associated with the health-related data that inform the hospitalization probability.

4. The system of claim 1, the operations further comprising:

determining a difference between (1) the hospitalization probability determined by the machine-learning model with respect to a portion of the people and (2) hospitalization events occurring with respect to the portion of the people; and wherein training the machine-learning model comprises training the machine-learning model based at least in part on the difference.

5. A method, comprising:

receiving, from a database and at a first time, data of a person;

determining a time interval for splitting the data into multiple records, wherein each of the multiple records corresponds to a second time that occurred before the first time;

generating, utilizing a first instance of the time interval, a first record including:

a first portion of the data attributable to the first instance of the time interval; and a first indication of whether an event occurred with respect to the person during the first instance of the time interval;

generating, utilizing a second instance of the time interval, a second record including:

a second portion of the data attributable to the second instance of the time interval; and a second indication of whether the event occurred with respect to the person during the second instance of the time interval;

dissociating the first record from the second record such that the first record and the second record are indicated as being independent of each other;

storing the first record and the second record such that the first record and the second record are indicated as being dissociated;

generating a machine-learning model configured to determine an event probability;

generating a training dataset configured to train the machine-learning model, the training dataset based at least in part on the dissociation of the first record and the second record, the health-related data, the first instance of the time interval, the second first instance of the time interval, the first record, and the second record;

training the machine-learning model utilizing the training dataset to identify trends between the dissociation of the first record and the second record, the health related data, the first instance of the time interval, the second first instance of the time interval, the first record, and the second record to determine if a hospitalization probability of a patient is improved;

determining, based at least in part on the trained machine-learning model, the event probability associated with a group of people; and ranking, utilizing the trained machine-learning model, individual people in the group of people based at least in part on the event probability.

6. The method of claim 5, further comprising:

identifying an event probability threshold;

identifying a portion of the group of people with event probabilities at or above the event probability threshold; and generating a recommendation for the portion of the group of people based at least in part on the event probabilities being at or above the event probability threshold.

7. The method of claim 5, wherein generating the machine-learning model comprises generating the machine-learning model based at least in part on features associated with the data that inform the event probability.

8. The method of claim 5, further comprising:

determining a difference between (1) the event probability determined by the machine-learning model with respect to a portion of the group of people and (2) event occurrences with respect to the portion of the group of people; and wherein training the machine-learning model comprises training the machine-learning model based at least in part on the difference.

9. The method of claim 5, wherein the machine-learning model is associated with an area-under-the-resource-operation-curve value of at least 0.81.

10. The method of claim 5, wherein generating the machine-learning model comprises generating the machine-learning model based at least in part on:
gradient boosting techniques; and
hyperparameter tuning of nodes associated with the event.

11. The method of claim 5, wherein input features are associated with the data, and wherein generating the machine-learning model comprises generating the machine-learning model based at least in part on:
identifying a first group of the input features that, when utilized by the machine-learning model, increase an accuracy of the machine-learning model;
identifying a second group of the input features that, when utilized by the machine-learning model, decrease the accuracy of the machine-learning model or maintain the accuracy of the machine-learning model; and
refitting the machine-learning model to utilize the first group of the input features and refrain from utilizing the second group of the input features.

12. The method of claim 5, further comprising:
identifying an event probability threshold;
identifying a portion of the group of people with event probabilities at or above the event probability threshold; and
causing the portion of the group of people to be accepted into a program based at least in part on the event probabilities being at or above the event probability threshold.

13. A system, comprising:
one or more processors; and
computer-readable media storing first computer-executable instructions that, when executed by the one or more processors, cause the one or more processors to perform operations comprising:
receiving, from a database and at a first time, health-related data of a person;
determining a time interval for splitting the health-related data into multiple records, wherein each of the multiple records corresponds to a second time that occurred before the first time;
generating, utilizing a first instance of the time interval, a first record corresponding to the person, the first record including a first indication of whether an event occurred with respect to the person during a first instance of the time interval;
generating, utilizing a second instance of the time interval, a second record corresponding to the person, the second record including a second indication of whether the event occurred with respect to the person during a second instance of the time interval;
dissociating the first record from the second record such that the first record and the second record are indicated as being independent of each other;
storing the first record and the second record such that the first record and the second record are indicated as being dissociated;
generating a machine-learning model configured to determine an event probability;
generating a training dataset configured to train the machine-learning model, the training dataset based at least in part on the dissociation of the first record and the second record, the health-related data, the first instance of the time interval, the second first instance of the time interval, the first record, and the second record;
training the machine-learning model utilizing the training dataset to identify trends between the dissociation of the first record and the second record, the health related data, the first instance of the time interval, the second first instance of the time interval, the first record, and the second record to determine if a hospitalization probability of a patient is improved;
determining, based at least in part on the trained machine-learning model, the event probability associated with a group of people; and
ranking individual people in the group of people based at least in part on the event probability and utilizing the trained machine-learning-model.

14. The system of claim 13, the operations further comprising:
identifying an event probability threshold;
identifying a portion of the group of people with event probabilities at or above the event probability threshold; and
generating a recommendation for the portion of the group of people based at least in part on the event probabilities being at or above the event probability threshold.

15. The system of claim 13, wherein generating the machine-learning model comprises generating the machine-learning model based at least in part on one or more machine learning techniques indicating features associated with first data associated with the person that inform the event probability.

16. The system of claim 13, the operations further comprising:
determining a difference between (1) the event probability determined by the machine-learning model with respect to a portion of the group of people and (2) event occurrences with respect to the portion of the group of people; and
wherein training the machine-learning model comprises training the machine-learning model based at least in part on the difference.

17. The system of claim 13, wherein the machine-learning model is associated with an area-under-the-resource-operation-curve value of at least 0.81.

18. The system of claim 13, wherein generating the machine-learning model comprises generating the machine-learning model based at least in part on:
gradient boosting techniques; and
hyperparameter tuning of nodes associated with the event.

19. The system of claim 13, wherein input features are associated with first data of the person, and wherein generating the machine-learning model comprises generating the machine-learning model based at least in part on:
identifying a first group of the input features that, when utilized by the machine-learning model, increase an accuracy of the machine-learning model;
identifying a second group of the input features that, when utilized by the machine-learning model, decrease the accuracy of the machine-learning model or maintain the accuracy of the machine-learning model; and
refitting the machine-learning model to utilize the first group of the input features and refrain from utilizing the second group of the input features.

20. The system of claim 13, the operations further comprising:
  identifying an event probability threshold;
  identifying a portion of the group of people with event probabilities at or above the event probability threshold; and
  causing the portion of the group of people to be accepted into a program based at least in part on the event probabilities being at or above the event probability threshold.

* * * * *